United States Patent [19]

Sheahon

[11] Patent Number: 4,961,430

[45] Date of Patent: Oct. 9, 1990

[54] CERVICAL BIOPSY INSTRUMENT

[76] Inventor: John Sheahon, U-2, Rte. 4, Lake Lotawana, Mo. 64063

[21] Appl. No.: 225,346

[22] Filed: Jul. 28, 1988

[51] Int. Cl.$^5$ .............................................. A61B 10/00
[52] U.S. Cl. .................................... 128/754; 606/171
[58] Field of Search .............. 128/749, 751, 754, 305; 606/167, 170, 171

[56] References Cited

U.S. PATENT DOCUMENTS

| | | | |
|---|---|---|---|
| 2,708,437 | 5/1955 | Hutchins | 128/751 |
| 2,728,357 | 1/1957 | Leibinger et al. | 128/751 |
| 2,994,321 | 8/1961 | Tischler | 128/305 |
| 3,327,702 | 6/1967 | DeMarco | 128/305 |
| 3,515,128 | 6/1970 | McElroy | 128/754; 606/171 |
| 3,606,878 | 10/1968 | Kellogg | 128/91 R |
| 4,099,518 | 7/1978 | Baghs et al. | 128/754 |
| 4,168,698 | 9/1979 | Ostergard | 128/751 |
| 4,651,753 | 3/1987 | Lifton | 128/751 |

FOREIGN PATENT DOCUMENTS 1116465  6/1968  United Kingdom ................ 128/752

*Primary Examiner*—Max Hindenburg
*Attorney, Agent, or Firm*—Michael Yakimo, Jr.

[57]                 ABSTRACT

A biopsy punch for extracting cervical tissue comprises a tubular housing having a cutting means slidable therethrough for slicing a strip of tissue from the cervix tip protruding into a tissue port. Three embodiments are presented illustrating various cutting edges for the cutting means. The first embodiment presents a bevelled cutting edge with piercing point for initially piercing the tissue. A second embodiment presents a mounting block for the cutting edge with the block key locked to the housing in slidable movement therethrough. A third embodiment presents a cylindrical cutting edge for providing a conical slice of biopsy tissue.

1 Claim, 5 Drawing Sheets

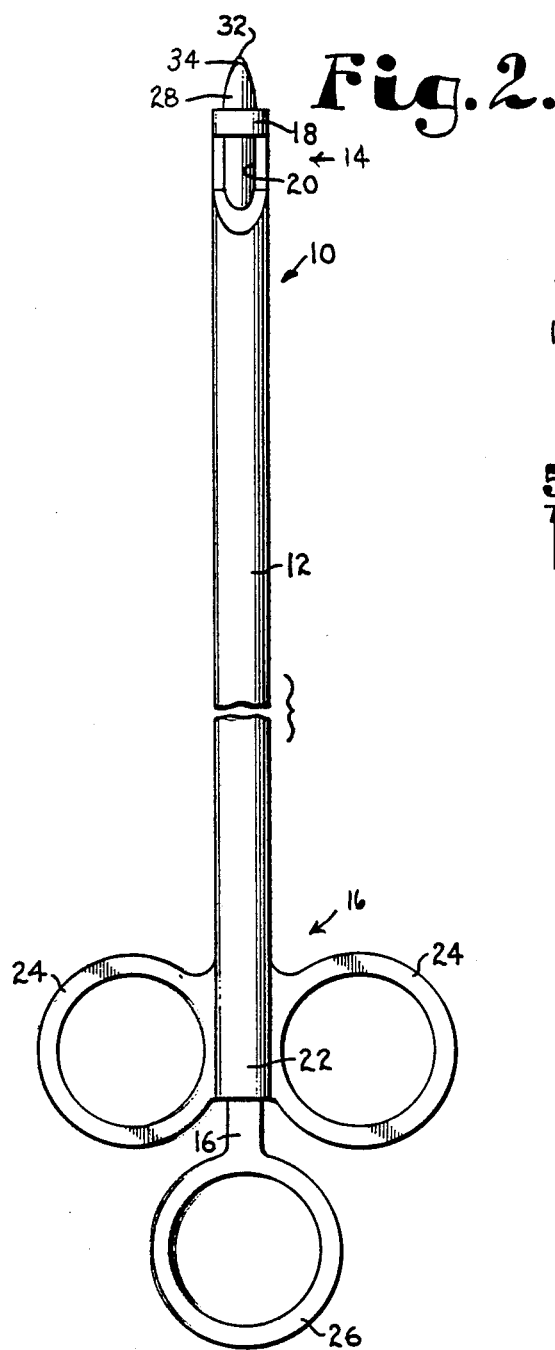
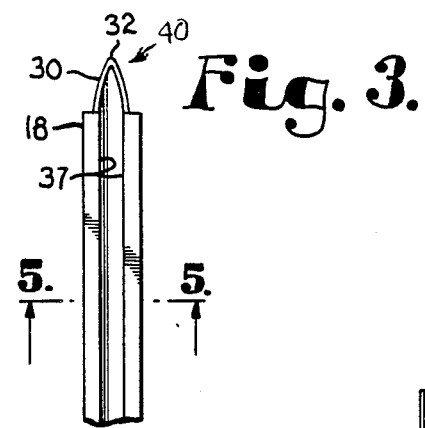
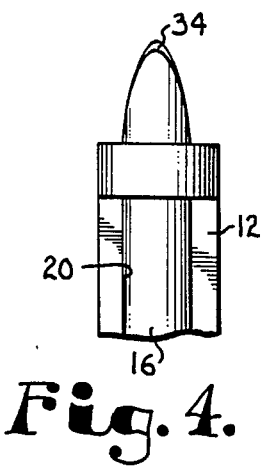
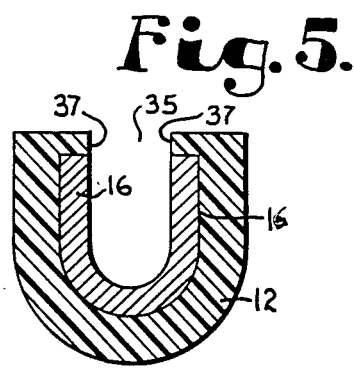
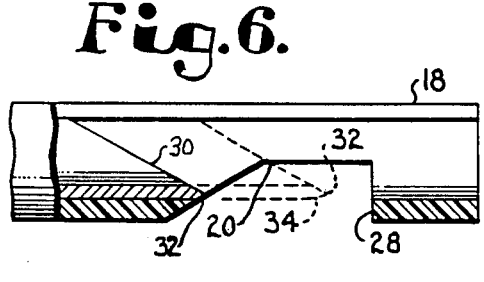
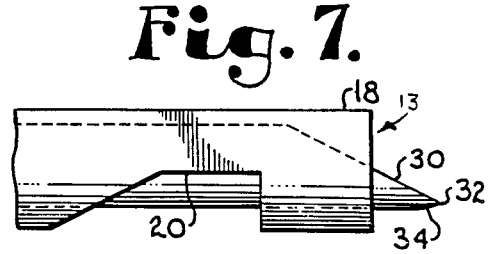

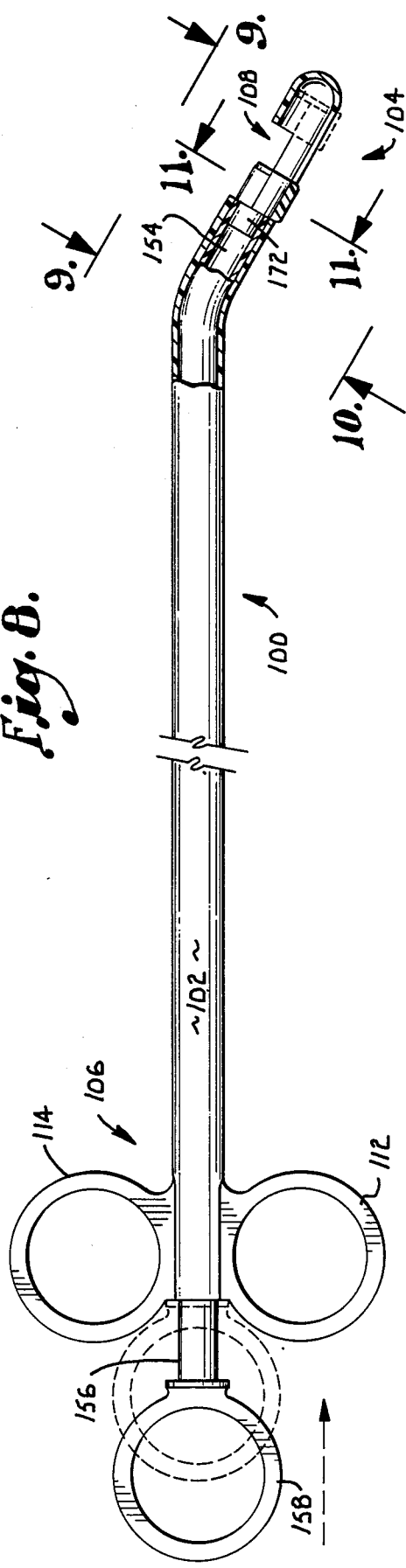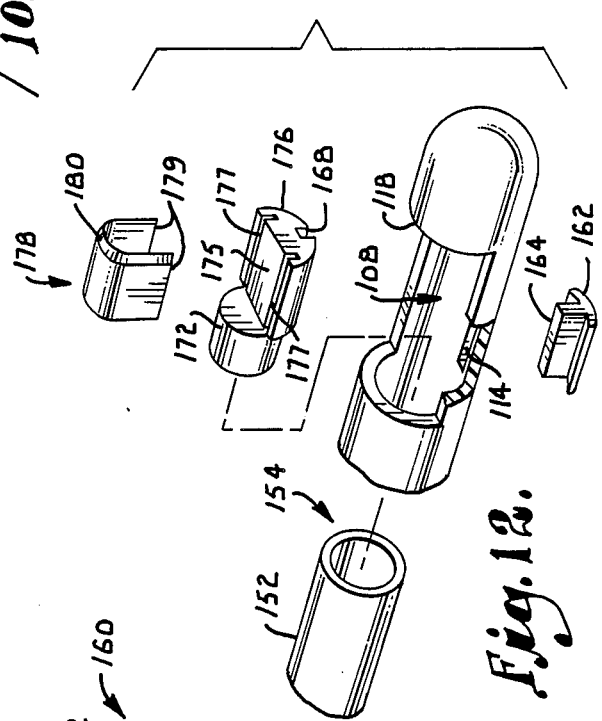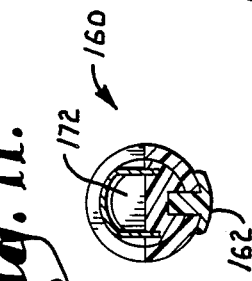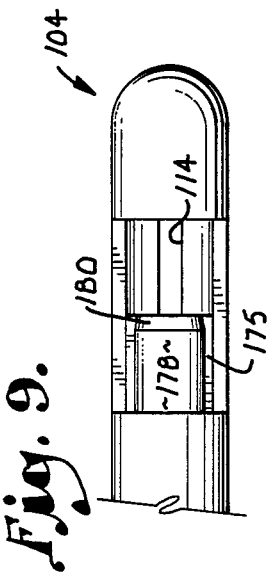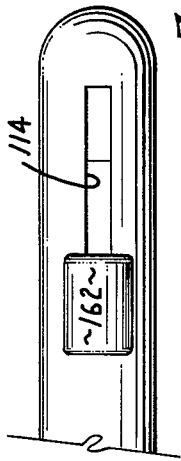

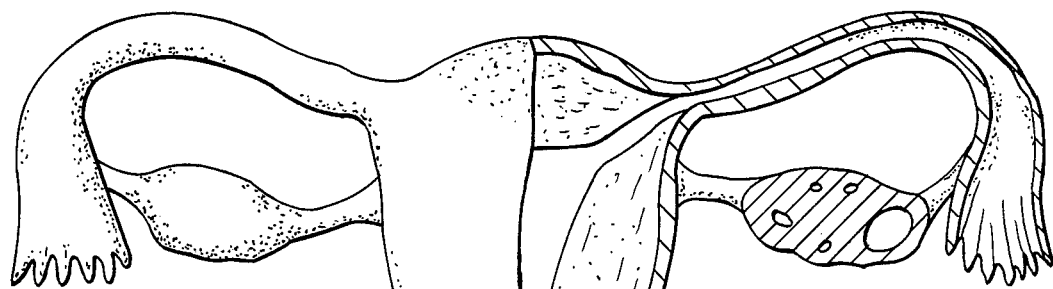
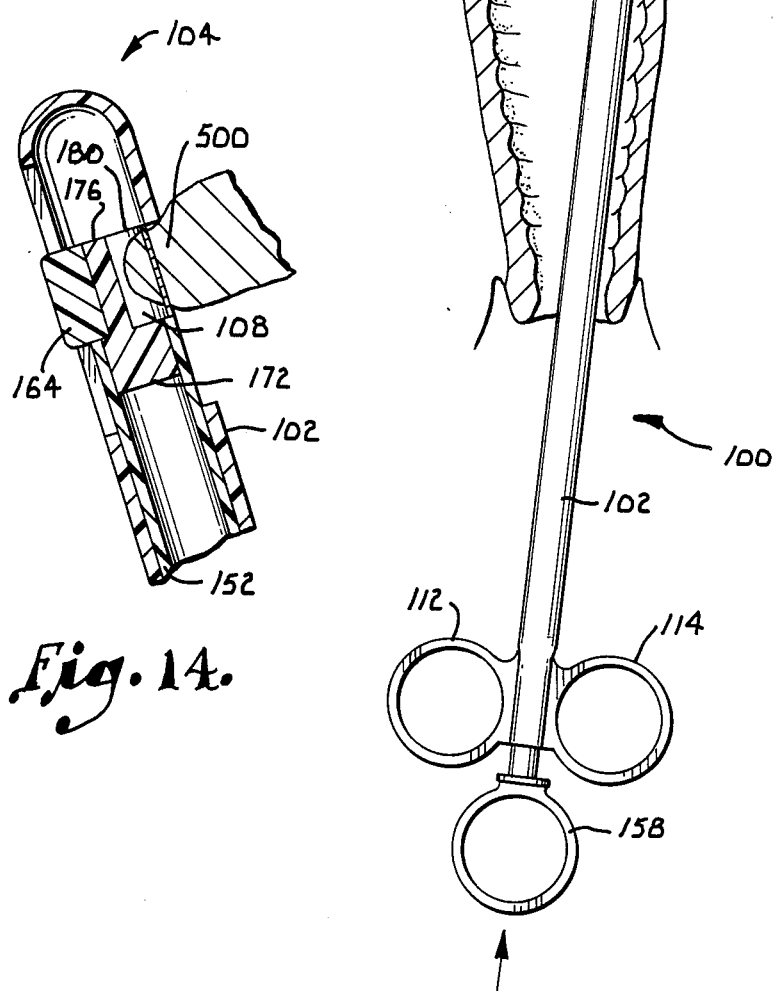
Fig. 13.
Fig. 14.

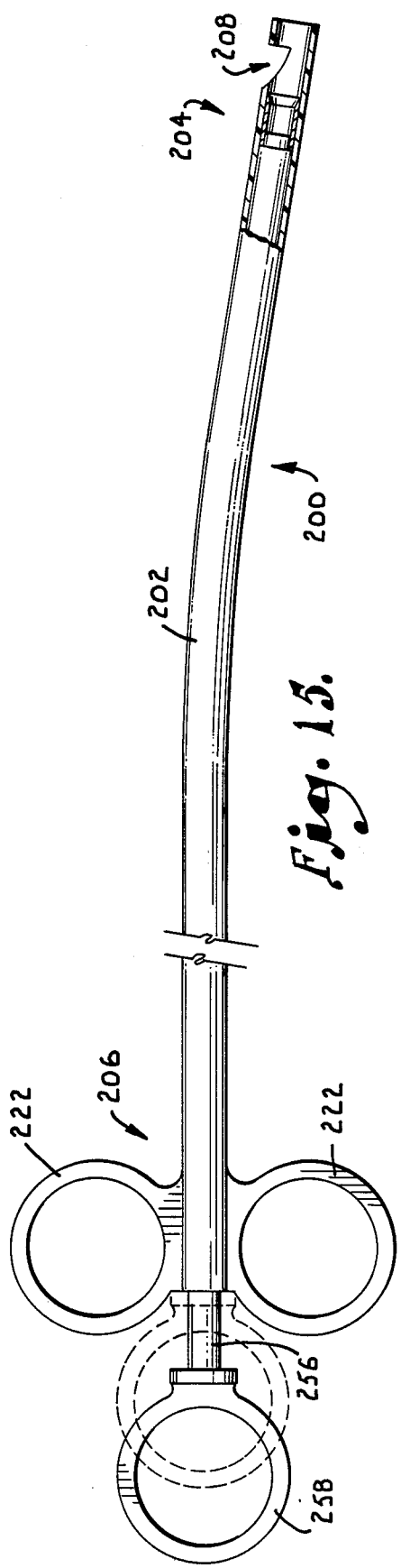
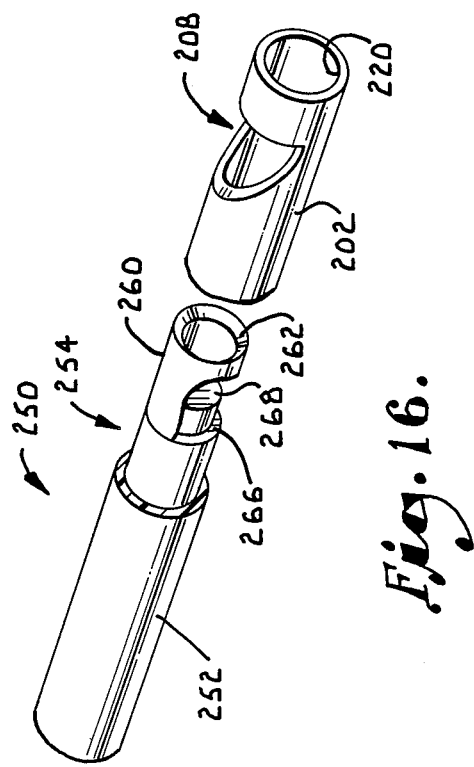
Fig. 15.
Fig. 16.

CERVICAL BIOPSY INSTRUMENT

BACKGROUND OF THE INVENTION

This invention relates to an instrument for extracting a biopsy specimen and more particularly to an instrument for conducting a cervical biopsy.

Various instruments in the prior art are known for extracting a biopsy section. A needle instrument for extracting biopsy sections is shown in U.S. Pat. No. 3,606,878. The specimen tissue is drawn by suction into an opening and severed by a slidable cutter. The suction is said to help retain the specimen in the cutter cup.

A double-sided biopsy knife is shown in U.S. Pat. No. 3,327,702 for obtaining biopsies of the cervix. The cutting blades are angled in a manner to provide a conical biopsy. Another biopsy punch is shown in U.S. Pat. No. 2,994,321. This punch utilizes opposing jaws having beaks which engage and grip a selected tissue portion therebetween. The closing of the jaws frees the tissue specimen from the surrounding tissue.

U.S. Pat. No. 2,778,357 illustrates a biopsy punch having first and second jaw members at one end thereof. Upon closing the jaws, the tissue is captured therebetween. A skin biopsy punch is shown in U.S. Pat. No. 3,515,128 which uses a knife in communication with a piston/cylinder assembly to hold the skin specimen by pressure differential upon such specimen being severed from the attached fatty tissue. Finally an endocervical strip biopsy instrument is disclosed in U.S. Pat. No. 4,168,698 which uses a basketlike member removably mounted onto a handle. The basket member carries a cutting blade which is drawn distally from the external os of the endocervical canel. During this withdrawal a strip of endocervical tissue falls into the basket.

Although these instruments are assumably effective in their operation, their design are relatively complex in construction and awkward in use. Moreover these previous devices have not been particularly designed for throw away after use and must be sterilized after extraction of the cervical tissue for subsequent use.

Accordingly I have provided cervical biopsy punches which are easy to manufacture, assemble and are specifically designed for obtaining a specimen of the cervical tissue with little or minimal discomfort to the patient. Moreover my now preferred punches being of an efficient design may be discarded after use precluding the need to subsequently sterilize the same.

Generally each of my punches comprise an elongated tubular housing having a slidable cutter blade therein. At the end of the tubular housing is a port designed to receive a portion of the cervical tissue therein. The end of the blade housing may be open so as to allow the cutting blade to extend beyond the housing upon completion of its extracting function and present the severed tissue specimen. At the proximal end of the housing is a handle for extension of the finger therethrough. A ring at the proximal end of the cutting blade receives the physician's thumb therethrough for exertion of pressure thereon and subsequent slidable movement of the cutting blade through the housing. Upon the slidable movement a portion of the cervical tissue extending into the port is severed and captured on the cutting blade.

Accordingly the general object of this invention is to provide a biopsy punch for extracting a cervical tissue specimen.

Another object of this invention is to provide a biopsy punch, as aforesaid, which is simple in construction and operation.

Still another object of this invention is to provide a cervical punch, as aforesaid, which presents a tissue receiving aperture therein for receiving the desired cervical tissue in position for subsequent extraction by the slidable blade.

A more particular aspect of certain embodiments of this invention is to provide a cervical punch, as aforesaid, which comprises an elongated blade housing having an opening at the distal end thereon with the extracted tissue specimen being presented beyond the blade housing.

Other objects and advantages of this invention will become apparent from the following description of various embodiments, the accompanying drawings and claims.

BRIEF DESCRIPTION OF THE DRAWINGS

FIG. 2 is a plan view of a first biopsy punch with the blade housing being foreshortened for purposes of illustration.

FIG. 3 is a plan view of the interior of the distal end of the biopsy punch of FIG. 1 and illustrates the relationship between the interior ledges of the housing and cutting blade.

FIG. 4 is an enlarged view of the distal end of the blade biopsy punch of FIG. 1 as extending through the tissue receiving aperture.

FIG. 5 is an enlarged sectional view, taken along line 5—5 in FIG. 3, illustrating the cooperation between the cutting blade and blade housing.

FIG. 6 is a side elevation view of the distal end of the biopsy punch with the distal end being broken away and sectioned to illustrate in solid lines the first position of the cutting blade within the housing and thereafter in phantom lines the cutting blade within the tissue aperture.

FIG. 7 is a side elevation view, similar to FIG. 6, illustrating the final position of the cutting blade in extension beyond the open distal end of the blade housing.

FIG. 8 is a plan view illustrating a second embodiment of the biopsy punch with a portion of the distal end broken away to illustrate the cooperation between the cutting member and tubular housing.

FIG. 9 is a view of the distal end of the biopsy punch, taken along lines 9—9 in FIG. 1, on an enlarged scale and illustrating the cutting edge/tissue receiving notch relationship.

FIG. 10 is an enlarged view of the distal end of the biopsy punch, taken along line 10-10 in FIG. 1, and illustrating the key lock engagement of the cutting member with the tubular housing.

FIG. 11 is a sectional view, taken along line 11—11 in FIG. 1, illustrating the keyed relationship of the cutting member with the distal end of the biopsy punch and the cutting blade with the mounting block.

FIG. 12 is an exploded view of the distal end of the biopsy punch and illustrates the relationship between the cutting blade and housing.

FIG. 13 is a diagrammatic view of the female internal accessory organs and illustrating the use of the biopsy punch of FIG. 8 for extracting cervical biopsy tissue.

FIG. 14 is a partial sectional view of the distal end of the biopsy punch of FIG. 13 on an enlarged scale and illustrating a portion of the cervical tissue therein for subsequent severance by the cutting blade.

FIG. 15 is a plan view illustrating another embodiment of the biopsy punch with a portion of the distal end broken away to illustrate the relationship between the cutting member and tubular housing.

FIG. 16 is a perspective exploded view, taken on an enlarged scale, and illustrating the relationship between the tubular cutting blade and blade housing.

DESCRIPTION OF THE PREFERRED EMBODIMENT(S)

Figure 1:
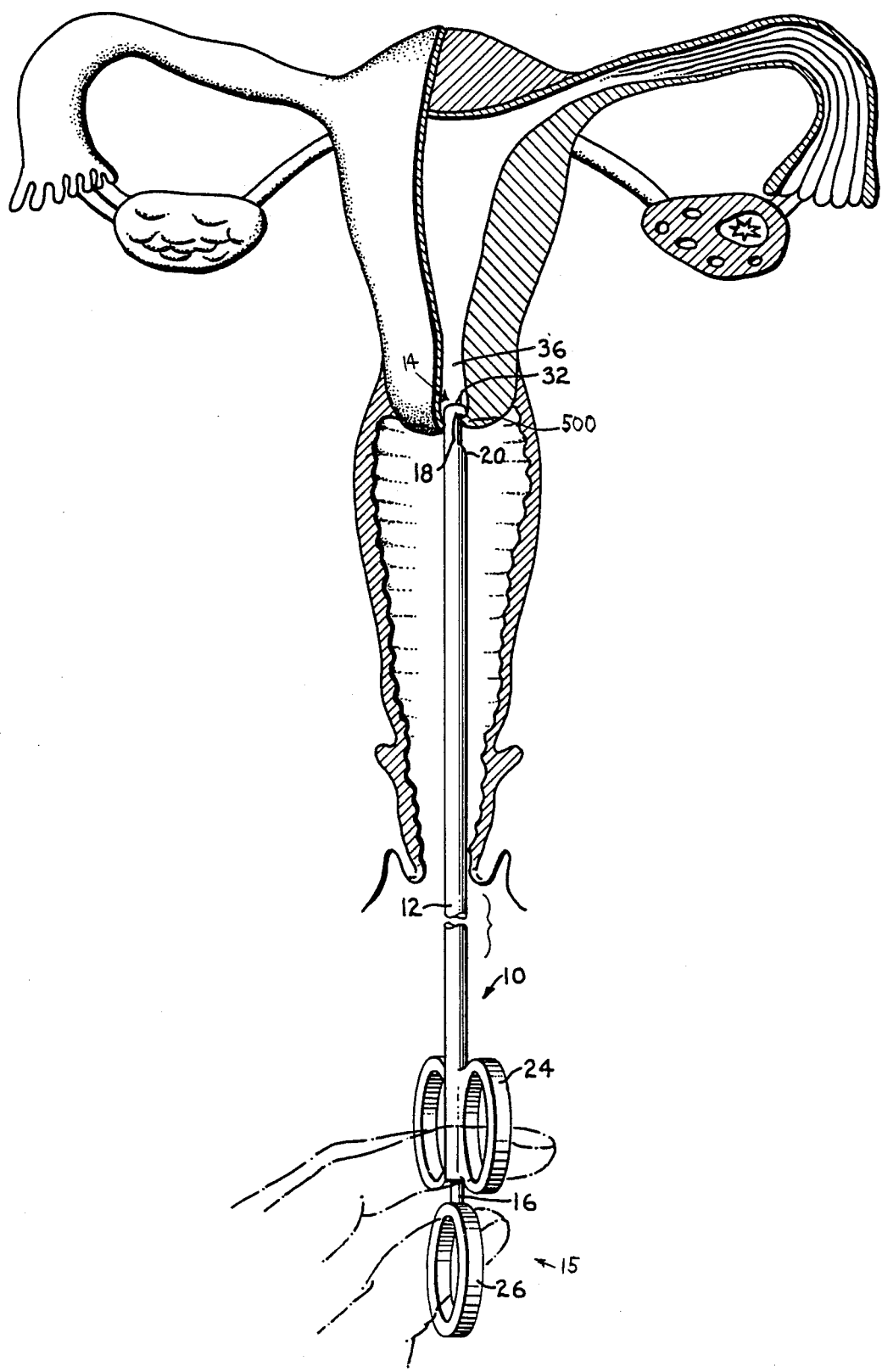
FIG. 1 is a diagrammatic view of the female internal accessory organs and showing a first embodiment of the biopsy punch in position for extracting cervical biopsy tissue.

Turning more particularly to the drawings, FIGS. 1-7 illustrates a first embodiment of the biopsy punch 10. This punch 10 comprises an elongated tubular housing 12 having a distal end 14 and a proximal end 15. At the distal end 14 is a tissue receiving port/aperture 20 for reception of a portion of the cervix 500 therein as shown in FIG. 1. The distal end 14 of the housing 12 presents an open end 13 for projection of the cutting blade 30 therethrough. Located at the proximal end 15 of the housing 12 are first and second guides 24 for insertion of the fingers of the user therethrough as shown in FIG. 1

As shown the cutting means comprises an elongated U-shaped tube 16, having a ring 26 at the proximal end thereof for insertion of the user's thumb therethrough as shown in FIG. 1. The distal end of said cutting means presents a beveled cutting blade 40. The beveled cutting blade 40 presents a piercing tip 32, beveled cutting edges 30 and an opposed beveled edge 34 rearwardly extending from the tip 32.

As best shown in FIG. 5 the interior of the tubular housing presents first and second inwardly extending lugs 37 which receives the U-shaped tube 16 of the cutting blade in nesting engagement therein. This relationship assures that the beveled cutting edge 30 of the cutting blade 40 do not wobble and are in the proper relationship, as shown in FIGS. 6 and 7, relative to the tissue receiving port 20. Otherwise upon insertion of the cutting member 40 within the housing 12 the beveled cutting edges 30 may face down in an improper position.

In operation the physician positions the punch in the vaginal canal position, as shown in FIG. 1, with the cervix 500 tip extending in tissue port 20. The cutting blade 40 is in the withdrawn position, i.e. to the proximal side of port 20, as shown in solid lines in FIG. 6. Upon thumb depression, the tip 32 of the blade initially pierces the cervical tissue with the subsequent bevel cutting edges 30 slicing off a strip of the cervical tissue. This slidable movement of the blade 40 is enhanced as the undersided edge 34 of the tip 32 is beveled to preclude the tip 32 from abutting the edge 28 of the housing 18 surrounding the tissue port 20. As shown in FIG. 7 the blade projects beyond the open end so as to present the tissue specimen to the user. This open distal end also precludes pressure back up within the housing and facilitates operation of the punch.

FIGS. 8-14 illustrate another embodiment of a biopsy punch 100. This embodiment 100 comprises a tubular housing 102 having an angled distal end 104 and a proximal end 106. At the distal end 104 is a tissue port 108 for entry of the cervix tip therein. (Although the distal end 104 of housing 102 is shown as closed, it may present an open aperture if desired). Located at the proximal end 106 of the tube 102 are a pair of guides 112 and 114 for insertion of the physician's fingers therethrough. Located on the underside of the distal end 104 and opposite said tissue port 108 is a key slot 114 for reception of a key tab 162 therein.

A cutting means 150 comprises an elongated, tubular shaft 152 having a distal end 154 and a proximal end 156. A ring 158 is located at the proximal end 156 for insertion of the physician's thumb therethrough. The shaft 152 is of a reduced diameter, relative to the inside diameter of the housing 102 so as to provide for relative sliding movement between the shaft 152 and housing 102.

At the distal end 154 of the shaft 152 is mounted a cutting blade assembly generally designated as 160. This assembly 160 includes a cylinder 172 which engages the distal end 152 of the shaft 152 via a nesting, friction fit engagement therebetween. The assembly 160 further comprises an attached, semi-circular mounting block 176 having longitudinal slots 177 longitudinally extending along the upper horizontal surface 175. A U-shaped cutting blade 178 has downwardly projecting edges 179 for engaging these slots 177 in a friction fit therebetween. A beveled front edge 180 presents the cutting edge. This bevel 180 precludes interference with the housing edge 118 defining the tissue port 108. As such the cutting blade 178 may be discarded and a new cutting blade insertable therein after use. This assembly 160 further comprises a key tab 162 having an upstanding wall 164 which is inserted through the slot 114 and engages a slot 168 in the underside of the housing 176. This relationship guides the cutting assembly in a desired longitudinal stroke during use.

As shown in FIGS. 13 and 14 this biopsy punch 100 is positioned so that a portion of the cervix 500 is protruding into the tissue port 108. The cutting edge 180 is initially upstream the port 108 with the thumb ring 158 being withdrawn to a displaced position as shown in solid lines in FIG. 8. This relationship is tactilely sensed by the user as the tab 162 abuts the proximal edge of slot 114. The physician extends his fingers through the guides 112, 114 and thumb through ring 158. Thumb pressure on the ring 158 causes a sliding motion of the shaft 152 through the housing 102. During this motion the beveled edge 180 of the blade 178 slices the cervical tissue depending through the port 108 which is captured on the blade 178.

During said sliding motion of the shaft 152 through housing 102 the key tab 162/slot 114 engagement precludes wobbling of the cutting blade 178. As such a more effective cut is achieved.

Another embodiment 200 of the biopsy punch is illustrated in FIG. 14. Again the punch 200 comprises an elongated housing 202 having an open distal end 204 and a proximal end 206. A tissue port 208 is located at the distal end 204 of the tube 102. An aperture 220 is located at the distal end 204 of the housing 202 for projection of the cutting blade 262 therethrough.

Finger rings 222 are located at the proximal end 206 of the housing 202 for projection of the physician's fingers therethrough.

A tubular cutting member 250 includes a shaft 252 slidable through the housing 202. The shaft 252 has a distal end 254 and a proximal end 256 with a thumb ring 258 at the proximal end 256 thereof.

At the distal end 254 of the shaft 252 is located a cylindrical stainless steel blade 260 housing a cylindrical cutting edge 262. The blade 262 is mounted to the distal end 254. The distal end 254 presents a shoulder 266 and a mounting tip 268 of reduced diameter to which the blade 260 is mounted thereon.

This embodiment 200 is used in a manner similar to the earlier discussed embodiments as shown in FIGS. 1-6 and FIGS. 714. The distal end 204 of the housing 202 is inserted in the vaginal canal so that the cervix tip 500 protrudes into the tissue receiving notch 208. The shaft 252 is in the solid line position (FIG. 15) such that the cutting edge 262 lies upstream the tissue port 208. Upon insertion of the cervix tip in port 208 the physician depresses the shaft 252 through the housing 202 by applying pressure on the thumb ring 258. A slice of the tissue is taken by the cutting edge 262 (preferably made of stainless steel) and presented to the physician upon extension of the cutting edge 262 through aperture 220 and beyond the end of the housing 202.

Although having described various embodiments herein such description is not considered to be limitations on my invention except as set forth in the following claims and functional equivalents thereof.

What I desire to claim by U.S. Letters Patent:

1. A biopsy punch comprising:
    an elongated housing having a distal end and a proximal end;
    handle means on said housing for grasping said housing;
    an elongated shaft having a configuration for slidable movement through said housing, said shaft having a distal end and a proximal end;
    a notch in said housing at the distal end thereof for receiving a portion of tissue desired for a biopsy specimen therein;
    an aperture at the distal end of said housing;
    a cylindrical cutting blade having a proximal and distal ends at the distal edge of said shaft;
    means for attaching said cylindrical cutting blade to the distal end of said shaft, said means comprising:
        an annular shoulder at the distal end of said shaft, said shoulder being of a reduced configuration relative to said shaft to provide a base for said proximal end of said cylindrical cutting blade; and
        a mounting tip extending from said shoulder, said mounting tip extending through said cylindrical cutting blade for a contiguous fit therewith, whereby to position said cutting blade at said distal edge of said shaft;
    means at the proximal end of said shaft for applying pressure thereon causing slidable movement of said shaft with cutting blade through said housing, said distal end of said cutting blade capturing a portion of tissue protruding into said notch during said sliding movement and presenting the same at said aperture located at said distal end of said housing.

* * * * *